United States Patent
Cao et al.

(10) Patent No.: US 8,694,097 B2
(45) Date of Patent: Apr. 8, 2014

(54) MULTI-CHANNEL SENSING METHODS IN IMPLANTABLE CARDIOVERTOR DEFIBRILLATORS

(75) Inventors: Jian Cao, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 475 days.

(21) Appl. No.: 12/826,880

(22) Filed: Jun. 30, 2010

(65) Prior Publication Data
US 2012/0004515 A1 Jan. 5, 2012

(51) Int. Cl.
*A61N 1/04* (2006.01)
(52) U.S. Cl.
USPC .......................................................... 607/14
(58) Field of Classification Search
None
See application file for complete search history.

(56) References Cited

U.S. PATENT DOCUMENTS

| | | | |
|---|---|---|---|
| 4,960,123 A | 10/1990 | Maker | |
| 5,117,824 A | 6/1992 | Keimel | |
| 5,365,932 A | 11/1994 | Greenhut | |
| 5,558,097 A | 9/1996 | Jacobson | |
| 5,564,430 A | 10/1996 | Jacobson | |
| 5,776,168 A | 7/1998 | Gunderson | |
| 6,393,316 B1 | 5/2002 | Gillberg | |
| 6,871,097 B1 | 3/2005 | Strandberg | |
| 7,167,747 B2 | 1/2007 | Gunderson | |
| 7,236,828 B2 | 6/2007 | Casavant et al. | |
| 7,266,409 B2 | 9/2007 | Gunderson | |
| 7,333,855 B2 | 2/2008 | Cao | |
| 7,403,813 B1 | 7/2008 | Farazi | |
| 2004/0015197 A1 | 1/2004 | Gunderson | |
| 2007/0038253 A1* | 2/2007 | Kim et al. | 607/4 |
| 2007/0276447 A1 | 11/2007 | Sanghera | |
| 2009/0018595 A1* | 1/2009 | Bharmi et al. | 607/14 |

FOREIGN PATENT DOCUMENTS

WO 2007027537 3/2007

OTHER PUBLICATIONS (PCT/US2011/042541) PCT Notification of Transmittal of the International Search Report and the Written Opinion of the International Searching Authority.

* cited by examiner

*Primary Examiner* — Carl H Layno
*Assistant Examiner* — Paula J Stice
(74) *Attorney, Agent, or Firm* — Michael C. Solder

(57) ABSTRACT

An implantable medical device uses an implantable sensor for acquiring a physiological signal that is received by a digital signal processor. The digital signal processor is a multi-channel signal processor including a first signal processing channel having a first sensitivity for sensing the physiological signal and a second signal processing channel having a second sensitivity different than the first sensitivity for sensing the physiological signal.

21 Claims, 7 Drawing Sheets

MULTI-CHANNEL SENSING METHODS IN IMPLANTABLE CARDIOVERTOR DEFIBRILLATORS

TECHNICAL FIELD

The disclosure relates generally to medical devices and, in particular, to an apparatus and method for multi-channel sensing of a physiological signal in a medical device.

BACKGROUND

Implantable cardioverter defibrillators (ICDs) typically sense a cardiac electrogram (EGM) signal using an intracardiac electrode for sensing cardiac signals (e.g. R-waves) and detecting arrhythmias. The sensitivity used for sensing cardiac event signals such as R-waves and fibrillation waves is typically set to a high sensitivity (i.e., a low setting, e.g. 0.3 mV) such that low amplitude fibrillation signals can be sensed. Such high sensitivity, however, can lead to oversensing of T-waves or other non-cardiac signals resulting in false detections of ventricular tachycardia or fibrillation. Reduced sensitivity to avoid oversensing, however, may result in undersensing of fibrillation signals. As such, a need remains for a method for cardiac signal sensing in ICDs that enables high sensitivity sensing for proper detection of arrhythmias while reducing the likelihood of oversensing that can lead to false arrhythmia detections.

DETAILED DESCRIPTION

Figure 1:
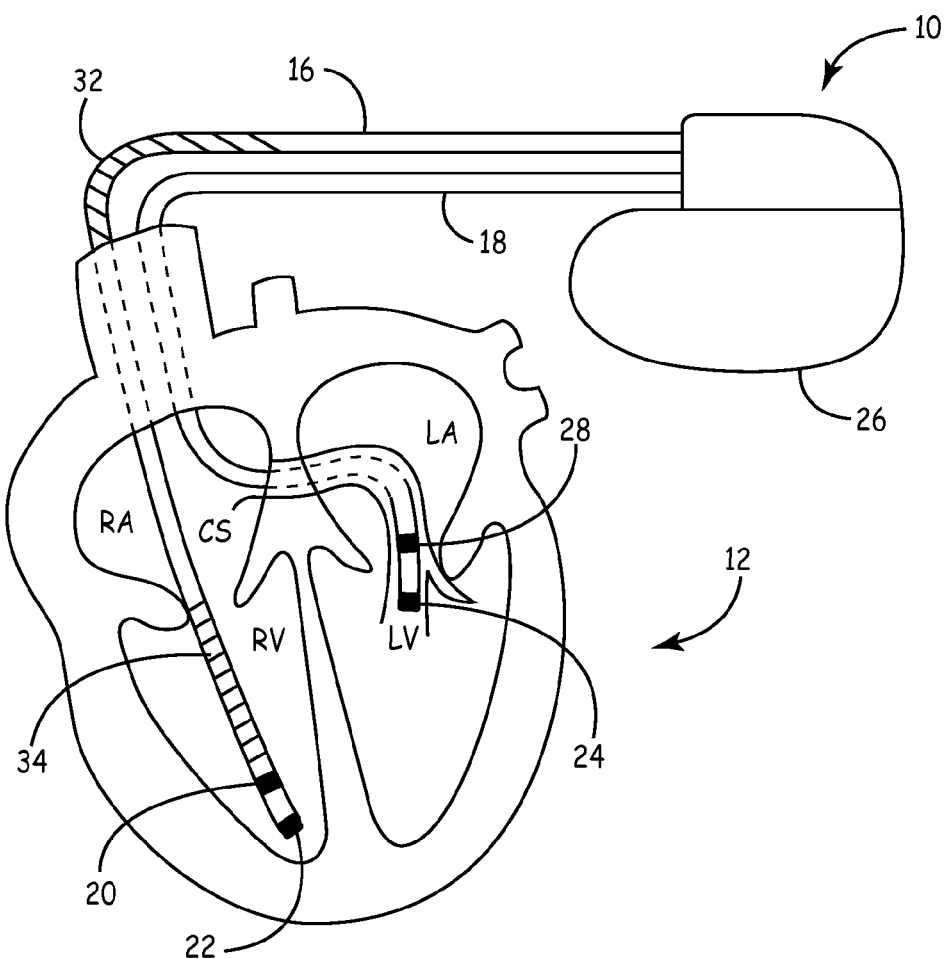
FIG. 1 is a schematic representation of an implantable medical device (IMD) coupled to a patient's heart.

In the following description, references are made to illustrative embodiments. It is understood that other embodiments may be utilized without departing from the scope of the disclosure. In some instances, for purposes of clarity, identical reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a schematic representation of an implantable medical device (IMD) 10 coupled to a patient's heart 12. While IMD 10 is embodied as an ICD in FIG. 1, methods described herein should not be interpreted as being limited to any particular implantable medical device or any particular cardiac medical device. Rather, embodiments may include any medical device that utilizes at least one physiological sensor for monitoring physiological events that may occur at time-varying rates and time varying signal amplitude. In the illustrative example, an electrode pair is used for sensing cardiac EGM or ECG signals, also referred to herein generally as "cardiac signals". Cardiac events, e.g. P-waves, R-waves and T-waves, may occur at varying rates and amplitudes depending on the prevailing heart rhythm.

Because the heart rhythm can change in an unpredictable manner, the rate and amplitude of cardiac events can vary in an unpredictable manner. In a patient that experiences both bradycardia and tachycardia, it is desirable to sense both low amplitude, high rate signals associated with tachycardia or fibrillation and higher amplitude, low rate signals associated with normal sinus rhythm or bradycardia. As such, monitoring cardiac events, which can vary in both rate and amplitude, provides a useful example for the application of the signal processing apparatus and associated methods described herein. The apparatus and methods described, however, may be adapted for use in any physiological monitoring application in which events sensed from a single physiological signal vary in amplitude over time depending on the state of a physiological condition. Other monitoring applications may include monitoring neural signals, respiratory signals, pressure signals, motion signals, or acoustical signals.

The sensitivity of a sensing circuit receiving a variable signal may sometimes be too sensitive, resulting in oversensing of events and at other times not sensitive enough to sense events of interest. Time varying signals produce a challenge in reliably sensing events for determining a physiological condition or need for therapy. In the example of cardiac signal sensing, depending on the sensitivity of the sensing circuit, low amplitude fibrillation signals may be undersensed if the sensing circuit sensitivity is too low (a high value in mV for the sensitivity setting), and T-waves, muscle artifact, or non-physiological noise may be oversensed if the sensitivity is too high (a low value in mV for the sensitivity setting).

In FIG. 1, the right atrium (RA), left atrium (LA), right ventricle (RV), left ventricle (LV), and the coronary sinus (CS), extending from the opening in the right atrium to form the great cardiac vein, are shown schematically in heart 12. Two transvenous leads 16 and 18 connect IMD 10 with the RV and the LV, respectively. Each lead includes at least one electrical conductor and pace/sense electrode. For example, RV lead 16 carries ring electrode 20 and tip electrode 22, and CS lead 18 carries ring electrode 28 and tip electrode 24. In addition, a housing electrode 26 can be formed as part of the outer surface of the housing of the device 10. The pace/sense electrodes 20, 22, and 24, 28 and housing electrode 26 can be selectively employed to provide a number of unipolar and bipolar pace/sense electrode combinations for pacing and sensing functions.

Typically, in pacing systems of the type illustrated in FIG. 1, the electrodes designated herein as "pace/sense" electrodes are used for both pacing and sensing functions. In certain embodiments, these electrodes can be used exclusively as pace or sense electrodes in programmed or default combinations for sensing cardiac signals and delivering pacing pulses. The leads and electrodes described can be employed to record cardiac signals. The recorded data can be periodically transmitted to a programmer or other external device enabled for telemetric communication with the IMD 10.

An RV coil electrode 34 and a superior vena cava (SVC) coil electrode 32 are also shown as being coupled to a portion of RV lead 16. Coil electrodes can additionally or alternatively be coupled to portions of CS lead 18. The coil electrodes 32 and 34, or other similar electrode types, can be electrically coupled to high voltage circuitry for delivering high voltage cardioversion/defibrillation shock pulses. Furthermore, coil electrodes 32 and 34 are available for use in combination with any other of the pace/sense electrodes 20, 22, 24 and 28 for bipolar sensing of cardiac signals. For example cardiac signals may be sensed using the RV tip electrode 22 paired with the RV coil electrode 34, referred to as a tip-to-coil sensing vector. The RV ring electrode 20 may be paired with the RV coil electrode 34, referred to as a ring-to-coil sensing vector.

Electrodes shown in FIG. 1 can be disposed in a variety of locations in, around, and on the heart and are not limited to the locations shown. Furthermore, other lead and electrode systems may be substituted for the system shown in FIG. 1. IMD 10 is shown coupled only with ventricular leads 16 and 18 but implementation of the sensing methods described herein is not limited to systems employing only ventricular leads. In other embodiments, single chamber atrial systems, dual chamber or multi-chamber systems may be used which include atrial leads used to position electrodes in, on or around the atrial chambers. In atrial sensing applications, P-waves and/or far-field R-waves may be sensed from an atrial sensing vector signal.

ICDs and pacemakers typically use a single ventricular EGM signal, typically the RV tip-to-ring or RV tip-to-coil, to sense ventricular events (R-waves) for determining a need for pacing and for detecting RR intervals meeting ventricular tachycardia or fibrillation (VT/VF) detection criteria. An EGM sensing vector may be a unipolar or bipolar sensing vector using one or two electrodes, respectively, placed in or on the ventricular heart chambers. Sensing errors that may occur on a single ventricular EGM signal may result in unneeded therapies being delivered by the ICD. Typical sensing errors that may occur include oversensing of T-waves, electromagnetic interference, non-cardiac myopotential noise, lead-related artifact, or other non-physiologic noise and double sensing of a single QRS complex. Sensing errors may also include undersensing of true depolarizations or fibrillation waves, leading to an underdetection of ventricular arrhythmias.

In the illustrative embodiment shown in FIG. 1, a single sensing vector may be obtained by using any of the electrodes 20, 22, 24, 28, 32 and 34 in bipolar pairs or in a unipolar combination with the housing electrode 26. Typically, a near field signal obtained by selecting any two of the electrodes 20, 22, 24, 28 and 34 located within the ventricles in a bipolar pair is used in an ICD for RR interval-based detection of ventricular tachycardia (VT) or ventricular fibrillation (VF). As will be described herein, if the sensed signal from one sensing vector becomes unusable, a sensed signal from another sensing vector may be selected.

Embodiments described herein are not limited to use with intracardiac or transvenous leads. Subcutaneously implanted electrodes used for sensing subcutaneous ECG signals may be used. Furthermore, other types of implantable physiological sensors may be included in IMD 10, carried by a lead extending from IMD 10, or in telemetric communication with IMD 10. Other physiological sensors may be used for acquiring time-varying signals used for sensing events and detecting physiological conditions. Other sensors that may be used in conjunction with IMD 10 include a pressure sensor, a motion sensor (e.g., an accelerometer), an acoustical sensor, or a chemical sensor (e.g. pH, oxygen saturation, glucose or the like).

Figure 2:
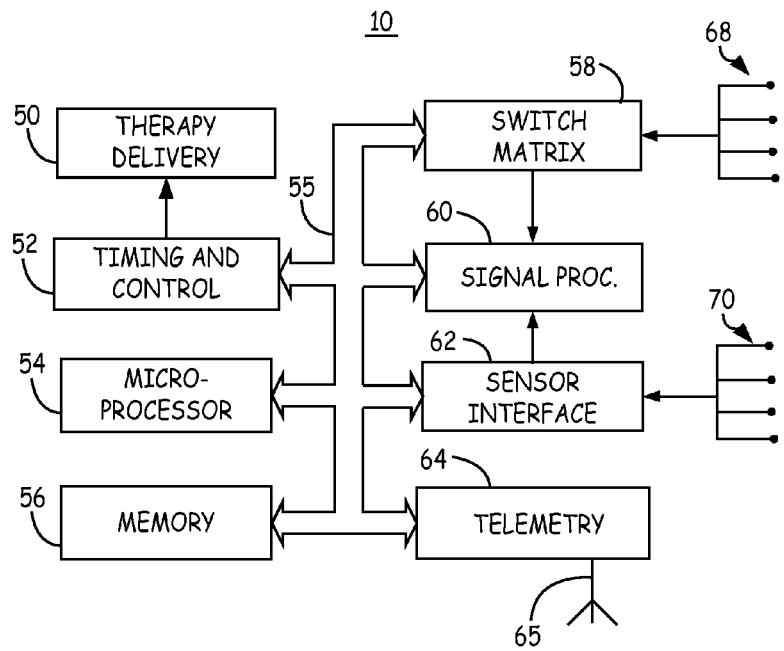
FIG. 2 is a functional block diagram of the IMD shown in FIG. 1 according to one embodiment.

FIG. 2 is a functional block diagram of the IMD 10 shown in FIG. 1 according to one embodiment. IMD 10 generally includes timing and control circuitry 52 and a controller that may be embodied as a microprocessor 54 or a digital state machine for timing sensing and therapy delivery functions in accordance with a programmed operating mode. Microprocessor 54 and associated memory 56 are coupled to the various components of IMD 10 via a data/address bus 55. IMD 10 includes therapy delivery module 50 for delivering electrical stimulation pulses to a patient's heart including cardiac pacing pulses, arrhythmia pacing therapies such as anti-tachycardia pacing (ATP) and cardioversion/defibrillation shocks, under the control of timing and control 52 and microprocessor 54. Therapy delivery module 50 is typically coupled to two or more electrodes 68 via an optional switch matrix 58. Electrodes 68 correspond to the various electrodes shown in FIG. 1. Switch matrix 58 is used for selecting which electrodes and corresponding polarities are used for delivering electrical stimulation pulses. In other embodiments, therapy delivery module may deliver electrical stimulation pulses to a nerve or may include a catheter and fluid delivery pump for delivering a therapeutic fluid.

Cardiac electrical signals are sensed for determining when an electrical stimulation therapy is needed and in controlling the timing of stimulation pulses. Electrodes used for sensing and electrodes used for stimulation may be selected via switch matrix 58. When used for sensing, cardiac signals received by electrodes 68 are provided to signal processing circuitry 60 via switch matrix 58. Signal processor 60 includes an analog-to-digital (A/D) converter and a digital signal processor and may include one or more amplifiers, filters, rectifiers or other signal processing modules for processing the received cardiac signal(s) for sensing cardiac events. Sensed cardiac events are then used by microprocessor 54 for detecting physiological conditions, such as detecting and discriminating cardiac arrhythmias, and by timing and control 52 for controlling therapy delivery as needed. For example, signal processor 60 includes cardiac event sensors for sensing ventricular events, i.e. R-waves, for use in determining R-R intervals (RRIs) and QRS waveform morphology which are in turn used by VT/VF detection algorithms implemented in microprocessor 54 and associated memory 56.

IMD 10 may additionally be coupled to one or more physiological sensors 70 carried by leads extending from IMD 10 or incorporated in or on the IMD housing. Signals from sensors 70 are received by a sensor interface 62 which provides sensor signals to signal processor 60. Signal processor 60 processes the signals to detect events which can be used by microprocessor 54 for detecting physiological conditions.

The operating system includes associated memory 56 for storing a variety of programmed parameter values that are used by microprocessor 54 in controlling IMD function. The memory 56 may also be used for storing data compiled from sensed physiological signals and/or relating to device operating history for telemetry out on receipt of a retrieval or interrogation instruction.

IMD 10 further includes telemetry circuitry 64 and antenna 65. Programming commands or data are transmitted during uplink or downlink telemetry between IMD telemetry circuitry 64 and external telemetry circuitry included in a programmer or monitoring unit.

Figure 3:
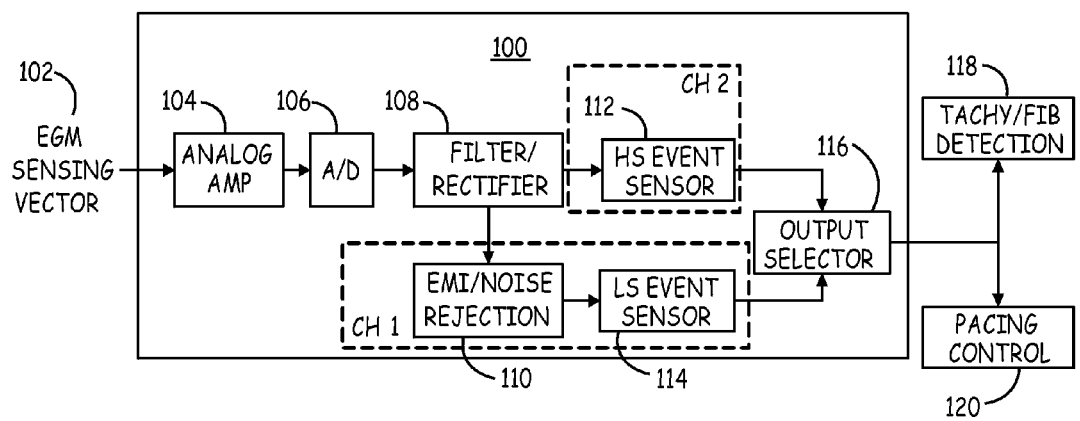
FIG. 3 is a functional block diagram of a signal processing module for use in an IMD.

FIG. 3 is a functional block diagram of one embodiment of signal processing components for use in an IMD. Signal processor 100 receives a cardiac signal 102 from an EGM sensing vector. The cardiac signal 102 may be pre-amplified by an analog amplifier 104 before undergoing conversion to a digital signal by ND convertor 106.

The digital signal is filtered and rectified at block 108 to enable sensing of cardiac events by event sensors 112 and 114. The filtered, rectified digital signal may be provided directly to a high sensitivity (HS) event sensor 112. The filtered, rectified digital signal may undergo additional filtering for removing electromagnetic interference (EMI) or other non-physiological noise by EMI/noise rejection block 110. The filtered signal is then provided to a low sensitivity (LS) event sensor 114.

The HS event sensor 112 is provided with a sensitivity higher than the LS event sensor 114. For example, HS event sensor 112 may be provided with a sensitivity less than approximately 0.6 mV, e.g., approximately 0.3 mV, and LS event sensor 114 may be provided with a sensitivity of greater than 1.0 mV, e.g. approximately 1.2 to 2.0 mV. The sensitivities of the HS and LS event sensors 112 and 114 may be programmable settings. Each event sensor 112 and 114 includes a sense amplifier for sensing cardiac events, which may use a fixed or an auto-adjusting threshold. An auto-adjusting threshold is generally disclosed in U.S. Pat. No. 5,117,824 (Kiemel, et al.), hereby incorporated herein by reference it its entirety.

Briefly, an event sensor 112 or 114 establishes an auto-adjusting sensing threshold as a predetermined proportion of the amplitude of a sensed event (e.g. R-wave or P-wave). The sensing threshold decays over a period of time thereafter, e.g. approximately 3 seconds or less, to a fixed, lower threshold level. The event sensor 112 or 114 is used to provide output signals indicative of the occurrence of R-waves (or P-waves or other physiological events being sensed by a given sensor). The event sensor output signals may be used for resetting pacing timing intervals (commonly referred to as escape intervals) by pacing control 120, and may be used as an input to the tachycardia/fibrillation detection module 118.

As can be seen in FIG. 3, a single physiological signal, in this case an EGM signal, is provided to a digital signal processor 100 for processing by two separate processing "channels", which are distinguished by different sensitivities of respective sensors. The LS event sensor 114, in combination with noise rejection 110, may be considered a first processing channel. HS event sensor 112 may represent a second processing channel. The two channels each receive the output from filter/rectifier block 108. Alternatively, each channel may include its own filter/rectifier and/or other signal conditioning components, for filtering the digitized signal prior to its respective LS event sensor or HS event sensor.

Digital signal processing techniques implemented in fully implantable systems provide the ability to process a single physiological signal simultaneously by multiple sensing circuit channels without excessive processing power requirements and drain on the IMD battery. Multi-channel signal processing allows events to be sensed from the time-varying physiological signal using different sensitivities simultaneously. While two channels are shown in FIG. 3, it is contemplated that more than two channels may be provided to process a single physiological signal using different sensitivities. Each channel may further be distinguished by different filtering properties as shown in FIG. 3.

The sensed event signals provided by the event sensors 112 and 114 are analyzed to determine which processing channel is providing the most reliable signals for use by different IMD functions at any given time. For example, the output of the HS event sensor 112 may provide a more desirable signal for use in detecting VT/VF while the output of the LS event sensor 114 may provide a more desirable signal for use in controlling pacing. As the EGM signal varies, with changing physiological conditions or changing interference or noise, however, the reliability of the event sensor output signals for use by different functions of the IMD may change. The output selector 116 allows the most appropriate event sensor output signals to be selected and used for different IMD functions. The selected event sensor output signal may be different for different IMD functions, and the selected output signal used for a given IMD function may change over time.

In one embodiment, output selector 116 receives the output of HS event sensor 112 and the output of LS event sensor 114 and selects which output is to be used by pacing control module 120 and which output is used by tachycardia/fibrillation detection module 118. Typically, the HS event sensor output will be used by detection module 118 because the higher sensitivity is needed for sensing low amplitude fibrillation waves. However, the output of the LS event sensor may at times be selected to be used alone or in combination with the HS event sensor output by detection module 118.

Figure 4:
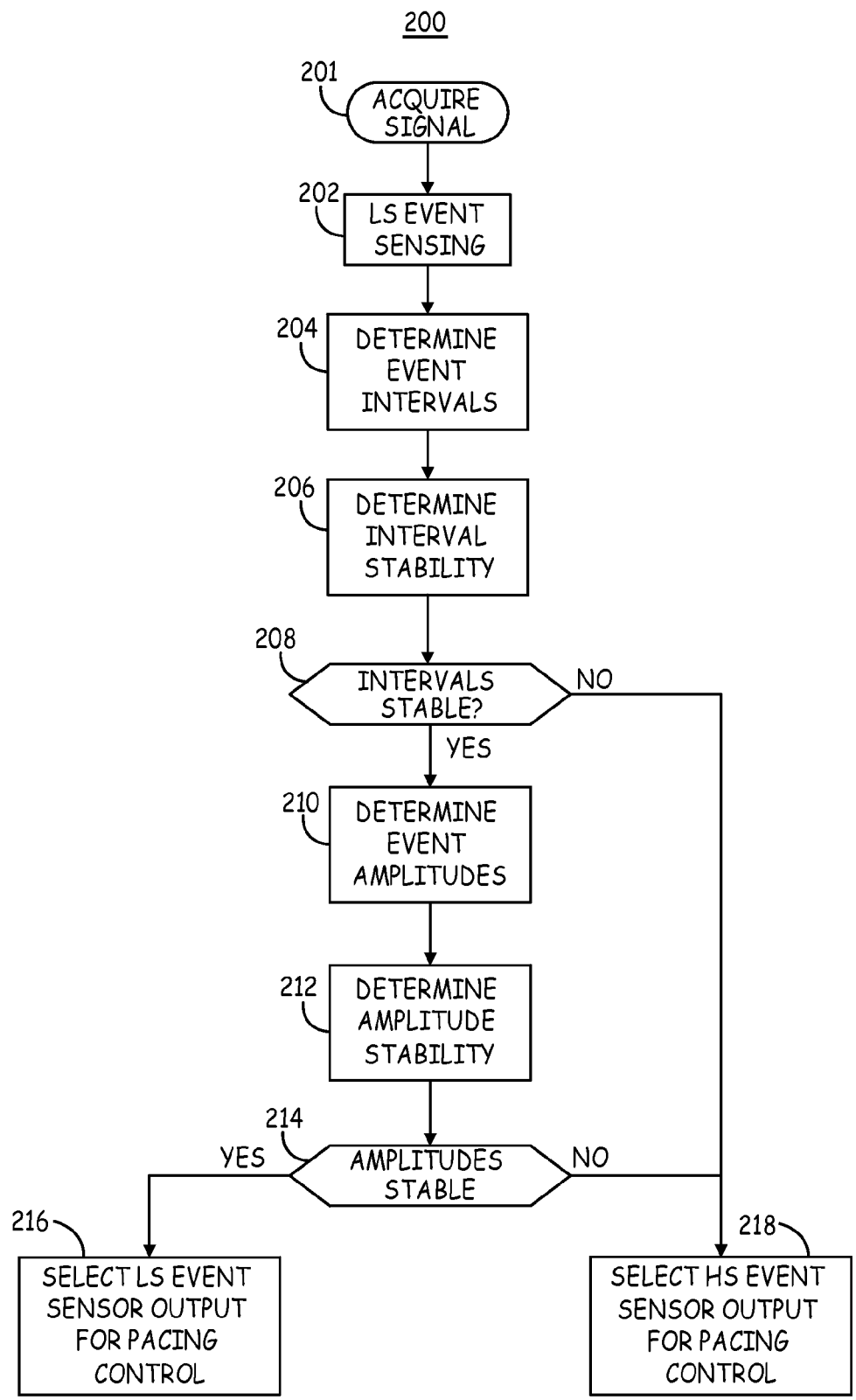
FIG. 4 is a flowchart of a method for selecting which output of a multi-channel signal processor is used by a therapy control module of the IMD.

FIG. 4 is a flowchart 200 of a method for selecting which output of a multi-channel signal processor is used by a therapy control module of the IMD. It is noted that the term "multi-channel" is sometimes used in the art to refer to a pacemaker or ICD that senses cardiac signals using more than one sensing vector, for example an "atrial channel" and a "ventricular channel" may refer to two different sensing vectors sensing cardiac signals in the atria and in the ventricles. As used herein, "multi-channel" signal processing refers to multiple signal processing channels applied to a single physiological signal acquired by a single sensor. In the illustrative embodiment, a bipolar or unipolar pair of electrodes is considered "a sensor" for sensing a cardiac signal, e.g. a ventricular or atrial EGM. The single cardiac signal received by the bipolar or unipolar pair of electrodes is provided to a multi-channel signal processing module as shown in FIG. 3. As such, the multi-channel signal processing refers to multiple parallel processing modules through which a single physiological signal is passed providing multiple output signals derived from the single physiological signal. This multi-channel processing of a single signal is in contrast to acquiring multiple signals using multiple sensors, wherein each signal is processed by a processing module producing one output signal for each sensed signal.

Flow chart 200 is intended to illustrate the functional operation of the device, and should not be construed as reflective of a specific form of software or hardware necessary to practice the methods described. It is believed that the particular form of software, hardware or firmware will be determined primarily by the particular system architecture employed in the device and by the particular detection and therapy delivery methodologies employed by the device. Providing software, hardware and/or firmware to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 201, a physiological signal is acquired and processed by a LS event sensor at block 202. The process shown in flowchart 200 is one method for selecting event sensor output signals for use by other IMD modules based on analysis of a LS event sensor output signal. It is to be understood that simultaneous event sensing using the HS event sensor may be occurring even though it is not explicitly shown in FIG. 4.

At block 204, sensed event intervals are determined. At block 206, the stability of the event intervals is computed. A metric of event interval stability may be defined in numerous ways. In one embodiment, a threshold event interval is established and a percentage of the measured event intervals that are longer than the established interval is determined. If the percentage of intervals that are greater than the threshold interval exceeds a predetermined stability threshold, for example approximately 80%, the event intervals may be considered to be occurring at a regular, slow rate that would correspond to a non-tachycardia rhythm. The threshold event interval may be a fixed or programmed interval or may be a varying interval computed based on one or more measured intervals. A fixed minimum threshold interval, e.g. corresponding to a tachycardia detection interval, may be defined.

If the intervals are not stable, as determined at block 208, based on the established interval threshold and stability criteria, the HS event sensor output is selected for use in pacing control at block 218. Large variation between event intervals or intervals that are shorter than the established threshold interval may indicate the presence of an arrhythmia. If the intervals are not stable, the HS event sensor is used by the pacing control to avoid undersensing of low amplitude R-waves or fibrillation waves that may be present.

If the intervals are stable, the process may go directly to block 216 to select the LS event sensor output for input to pacing control without further analysis of the sensed events. The intervals are considered to indicative of a slow and stable rate (i.e. non-tachycardia rate) that is reliable for controlling pacing pulses. The presence of undersensed events is considered unlikely if the intervals are regular as determined by the applied interval stability criteria. The HS event sensor output may still be provided as input for the tachycardia/fibrillation detector so that low amplitude signals may be detected for use in detecting tachycardia/fibrillation intervals.

In addition or alternatively to analyzing sensed event intervals, sensed event amplitudes may be analyzed at blocks 210 through 214 for use in selecting which processing channel output is used for pacing control. At block 210, sensed event amplitudes are measured. A peak detector may be included in the output selector for detecting signal peaks after an event is sensed as a result of the EGM signal crossing the sensing threshold. A number of peak amplitudes may be measured and compared to an amplitude threshold to determine the percentage of sensed signals having a peak amplitude greater than the threshold at block 212. The amplitude threshold may be a predetermined value, which may be fixed or programmable. The amplitude threshold may be set as a proportion of the programmed sensitivity of the LS event sensor.

Alternatively, the amplitude threshold may be computed using the measured peak amplitudes, e.g. as a proportion of an average of the measured amplitudes, a proportion of the nth largest amplitude, or another metric of the measured amplitudes. A minimum amplitude threshold may be predefined when a variable amplitude threshold is computed from measured amplitudes. The minimum amplitude threshold ensures that the peak amplitudes exceed at least some minimum threshold that is considered to be indicative of relatively large amplitude, stable R-waves.

At block 214, the percentage of peak amplitudes of sensed events crossing the amplitude threshold is compared to a stability threshold. If the amplitudes are found to be "large" as defined by the amplitude threshold and "stable" as defined by the stability threshold, the relatively large stable peak amplitudes of sensed events suggest a stable rhythm with a low likelihood of undersensed events. The LS event sensor output is selected for input to the pacing control module at block 216. As described above, the HS event sensor output may still be provided to the tachycardia/fibrillation detector such that low amplitude events associated with an arrhythmia may be detected.

If the sensed event amplitudes are not found to be large and stable, based on the amplitude threshold and stability threshold applied at blocks 212 and 214, the HS event sensor output is selected for use by pacing control at block 218. Low amplitude sensed events or variability between sensed event amplitudes suggests the possibility that low amplitude events may be occurring but are undersensed. In this case, the HS event sensor with nominal sensitivity of 0.3 mV, for example, may provide more reliable event sensing than the LS event sensor. The LS event sensor may effectively avoid or minimize oversensing issues (T-wave, noise, etc.) and deliver pacing therapy more effectively, which is important in pacemaker dependent patients.

As such, in some embodiments, the tachycardia/fibrillation detection module may always receive the HS event sensor output for detection of tachycardia/fibrillation episodes while the pacing control module may switch between receiving the LS event sensor output and the HS event sensor output depending on the analysis of the sensed event signals provided by LS event sensor.

In FIG. 4, an analysis of the event intervals is shown to occur first followed by an analysis of the event peak amplitudes. It is to be understood that the analysis could occur in the reverse order or simultaneously. In the various flowcharts and functional block diagrams presented and described herein, when multiple criteria are applied for selecting an output signal for use in controlling a device function, the criteria may be applied individually (a single criterion) or in any combination for the purposes of selecting the output signal. The order of applying multiple criteria may be changed from the particular order of applied criteria described in the flowcharts presented herein without adverse results. It is contemplated that where multiple criteria are described for controlling a particular device function, any subset or combination of those criteria may be applied and are not limited to being applied in any particular order.

Analysis of sensed event intervals and event amplitude are described above for use in selecting which signal processing channel output is used for controlling a device function. It is recognized that numerous event characteristics might be analyzed such as peak slope, slew rate, event width, or other event features, for determining if an event sensor output signal is the most reliable signal available for use in controlling a therapy or for detecting a physiological condition.

Figure 5:
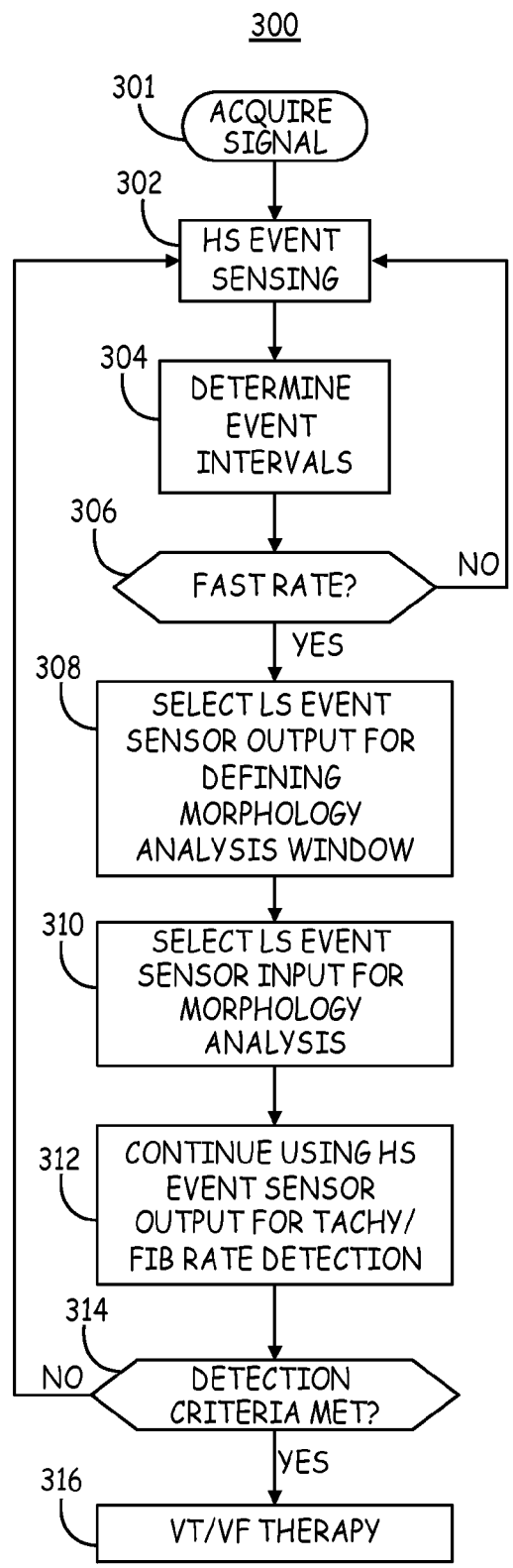
FIG. 5 is a flowchart of a method for selecting event sensor output for use in tachycardia/fibrillation detection in an ICD.

FIG. 5 is a flowchart 300 of a method for selecting event sensor output for use in tachycardia/fibrillation detection in an ICD. At block 301, an EGM signal is acquired and provided to the HS event sensor at block 302. It is to be understood, while not shown explicitly, in FIG. 5, that the same EGM signal may be simultaneously provided to the LS event sensor for performing the analyses described in conjunction with the flowchart 200 of FIG. 4. In other words, the output selector 116 may be selecting which of the HS event sensor output and the LS event sensor output is provided to pacing control 120 while also selecting when the tachycardia/fibrillation detection module 118 receives output from the HS event sensor 112, the LS event sensor 114 or both.

At block 304, sensed event intervals are measured between event signals provided by the HS event sensor. The intervals are compared to criteria for detecting a fast rate at block 306. For example, a fast rate may be detected when a required number of the most recent measured intervals are shorter than predefined tachycardia or fibrillation detection intervals. If a fast rate is not detected, the process returns to block 302 and continues HS event sensing.

When a fast rate is detected, QRS morphology analysis may be used to verify that the fast rate corresponds to VT or VF. One method of arrhythmia detection in an ICD using morphology analysis and template matching is generally described in U.S. Pat. No. 6,393,316 (Gillberg et al.), hereby incorporated herein by reference in its entirety. If morphology analysis is needed for detecting an arrhythmia episode, the LS event sensor output signal is selected as input to the tachycardia/fibrillation detection module at block 308.

The LS event sensor output provides sensed event signals that are used to define analysis windows encompassing a sensed event for performing morphology analysis of the QRS waveform. Additionally, the LS event sensor signal input which has undergone filtering for EMI rejection may be passed directly by the output selector 116 (FIG. 3) to the tachycardia/fibrillation detection module 118 at block 310 for use in computing a template of an unknown beat for comparison to a known morphology template. With the LS event sensor channel designed for optimal rejection of EMI and/or 50/60 Hz noise (e.g., using a low pass or notch filter), the LS event sensor channel is optimized for QRS sensing and thus provides an optimal signal for setting the morphology analysis window and for acquiring a signal morphology. If T-wave oversensing is occurring in the HS event sensor channel, signal morphology associated with sensed T-waves will not match a normal sinus rhythm template. By using the LS event sensor channel for setting a window for capturing EGM signal morphology from a selected sensing vector when a fast rate is detected, inappropriate tachycardia/fibrillation detection due to oversensing may be reduced. The EGM signal morphology may be captured during a morphology analysis window applied to any desired sensing vector, e.g., RV coil to ICD housing.

At block 312, the HS event sensor output continues to be used for detecting the tachycardia/fibrillation rate. At block 314, rate detection criteria applied to the HS event sensor output signal and morphology detection criteria applied using the LS event sensor output signal for setting morphology analysis windows are used to determine if tachycardia or fibrillation detection criteria are met. The detection criteria may vary between embodiments and may relate to detecting and discriminating different forms of VT and VF and discriminating VT/VF from supraventricular tachycardia (SVT).

If detection criteria are met, a VT/VF therapy may be delivered as needed at block 316, according to a programmed menu of therapies. If detection criteria are not met, the process returns to block 302 to continue monitoring the fast rate using the HS event sensor output signal. If a fast rate is no longer being detected as determined at block 306, the LS event sensor output signal is no longer selected for input to the tachycardia/fibrillation detection module.

Figure 6:
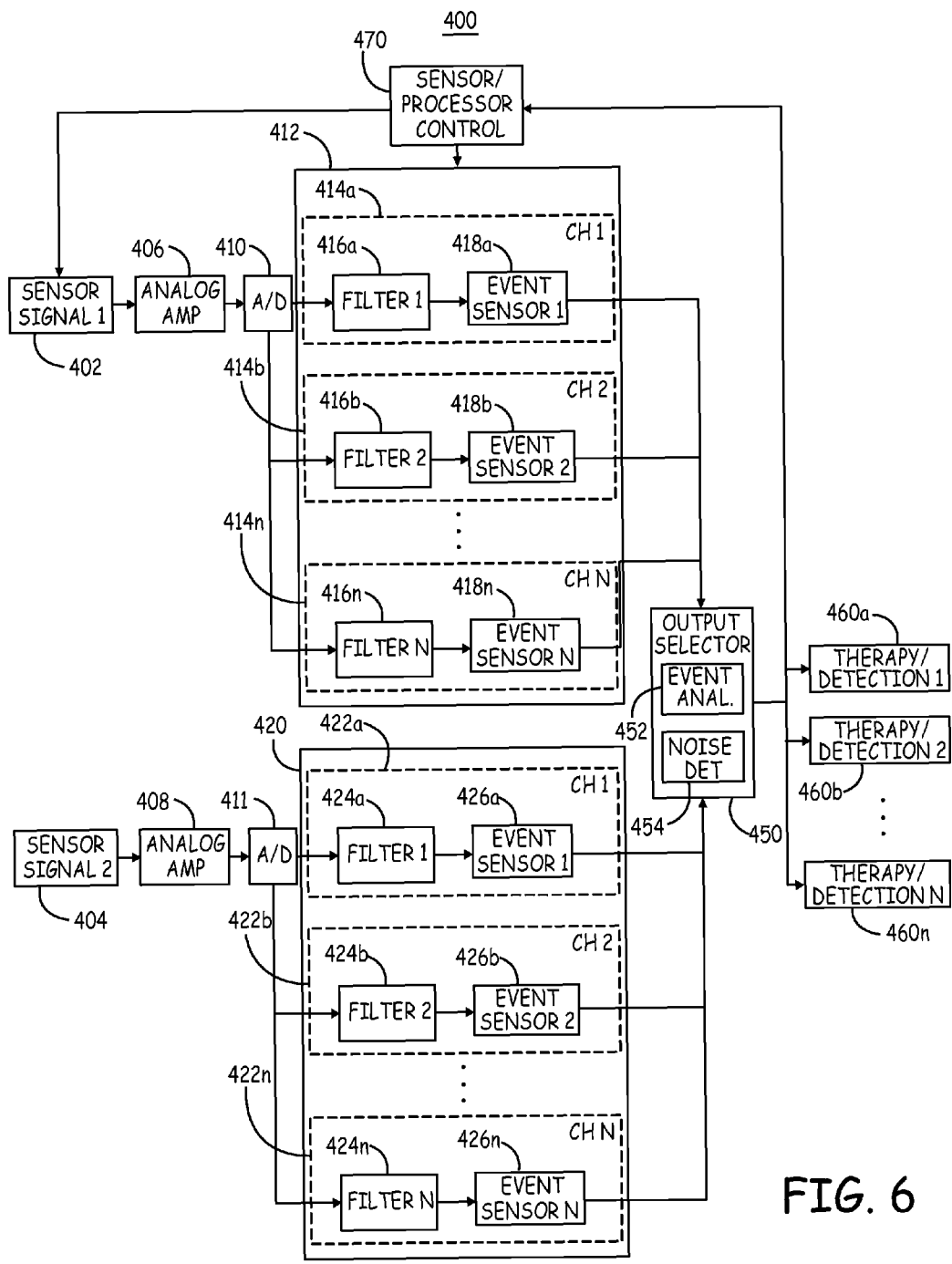
FIG. 6 is a functional block diagram of one embodiment of signal processing components of an implantable medical device.

FIG. 6 is a functional block diagram 400 of one embodiment of signal processing components of an implantable medical device. Two or more sensor signals 402 and 404 are received by respective analog amplifiers 406 and 408 and A/D convertors 410 and 411. Sensor signals 402 and 404 may correspond to different EGM sensing vectors, such as, but not limited to, tip-to-coil, tip-to-ring, ring-to-coil, and coil-to-can.

In other implementations, two or more acquired sensor signals 402, 404 are not limited to EGM signals nor limited to being the same type of signals. Other physiological signals listed herein may be acquired and provided as input to the signal processing blocks shown. Combinations of different sensor signals obtained by similar sensor types deployed at different body locations may be used. For example, EGM, blood pressure or heart wall motion signals sensed at different locations may be provided as the different sensor signals 402 and 404. In other embodiments, combinations of different types of physiological signals, for example combinations of electrical, pressure, acoustical, motion or other types of signals acquired by implantable medical sensors may be acquired as sensor signals 402, 404 in the multi-channel signal processing scheme shown in FIG. 6. In other words, the sensing scheme shown including multiple sensing channels for sensing different physiological signals in addition to the multi-channel signal processing described above. Each sensed physiological signal, is processed by a respective multi-channel signal processor.

After being converted to a digital signal, each physiological signal is processed by respective multi-channel signal processors 412 and 420. Digital signal processor 412 includes n channels, 414a through 414n (collectively 414). Each channel 414 is characterized by a distinct combination of filtering properties and channel sensitivity. As such, each filter 416a through 416n (collectively 416) may represent different filtering properties and/or each event sensor 418a through 418n (collectively 418) may represent different channel sensitivity. One channel 414a may provide high frequency EMI noise filtering (filter 416a) with low sensitivity (event sensor 418a). Another channel 414b may include a high pass filter 416b, e.g., a 20 Hz high pass filter, for T-wave rejection with a low sensitivity event sensor 418b. Another channel may provide 50/60 Hz filtering using a notch filter combined with low sensitivity event sensor. Yet another channel may provide a relatively lower-frequency high pass filter, e.g. an approximately 12-14 Hz high pass filter, with a high sensitivity event sensor. The outputs of each of the event sensors 418 are provided to output selector 450.

Similarly, each additional physiological sensor signal 404 is provided to a respective multi-channel digital signal processor 420 which includes n channels 422, each characterized by a distinct combination of filtering properties of filters 424 and sensitivity of event sensors 426.

The output selector 450 may choose any of the outputs from event sensors 418 and 426 of the different multi-channel processors 412 and 420 to provide a selected event sensor output signal as input to the various therapy control or physiological detection modules 460. Output selector 450 includes an event analyzer 452 for analyzing the amplitudes, event intervals, or other characteristics of sensed events from any given channel, as described above, for selecting an output signal for use by a particular therapy delivery or detection module 460.

The various modules 460 may be used for controlling different types of therapy provided by the IMD or for monitoring different physiological conditions detected by the IMD. Therapies may include cardiac pacing or shock pulses, delivery of a therapeutic fluid, neurostimulation or the like. Physiological conditions may relate to cardiac arrhythmias, heart failure conditions, respiratory conditions, syncope, diabetes, etc. At different times, the time-varying physiological signals 402, 404 may result in a different channel output signal being selected as the optimal signal for controlling a particular therapy and/or detecting a physiological condition.

In some embodiments, a dedicated sensor is used by a particular therapy/detection module 460. The output selector 450 then selects which output signal from the multi-channel processor associated with the dedicated sensor is provided to the particular therapy/detection module. A dedicated sensor may be used when the therapy/detection module requires a signal from a particular sensor type or from a particular location.

In other embodiments, two or more of the available sensors 402, 404 may be usable by a particular therapy/detection module 460. In this case, the output selector 450 may select an output signal provided to a particular therapy/detection module in a multi-step approach wherein one output signal corresponding to each sensor is selected from each multi-channel processor 412, 420 as preliminary output signals. A final output signal to be provided to the particular therapy/detection module 460 is selected from the preliminary output signals. As such, the signal used by a particular therapy/delivery module 460 may change over time between different output signals of different multi-channel processors 412, 420 (associated with more than one sensor).

Output selector 450 may further include a noise detector 454 for detecting lead or sensor-related noise in an acquired signal in response to the sensed event analysis. The output selector may reject particular sensor signals based on the analysis of sensed events. If one sensor signal is determined to include lead-related noise or other types of noise related to lead or sensor performance, the sensor may be rejected for use in detection and therapy control. Sensor/processing control module 470 may receive control signals from output selector 450 for selecting which sensor signals are acquired and received by the multi-channel signal processor.

For example if an RV lead carrying multiple electrodes, e.g. a tip, ring and coil electrode, results in significant lead-related artifact in a tip-to-coil sensing vector, the output selector 450 may select an event sensor output obtained using a ring-to-coil EGM signal. The sensor control 470 may respond to the rejection of this signal by selecting a different sensing vector or cancelling or turning off signal processing of the rejected signal by the respective multi-channel processor receiving the rejected sensor signal.

Figure 7:
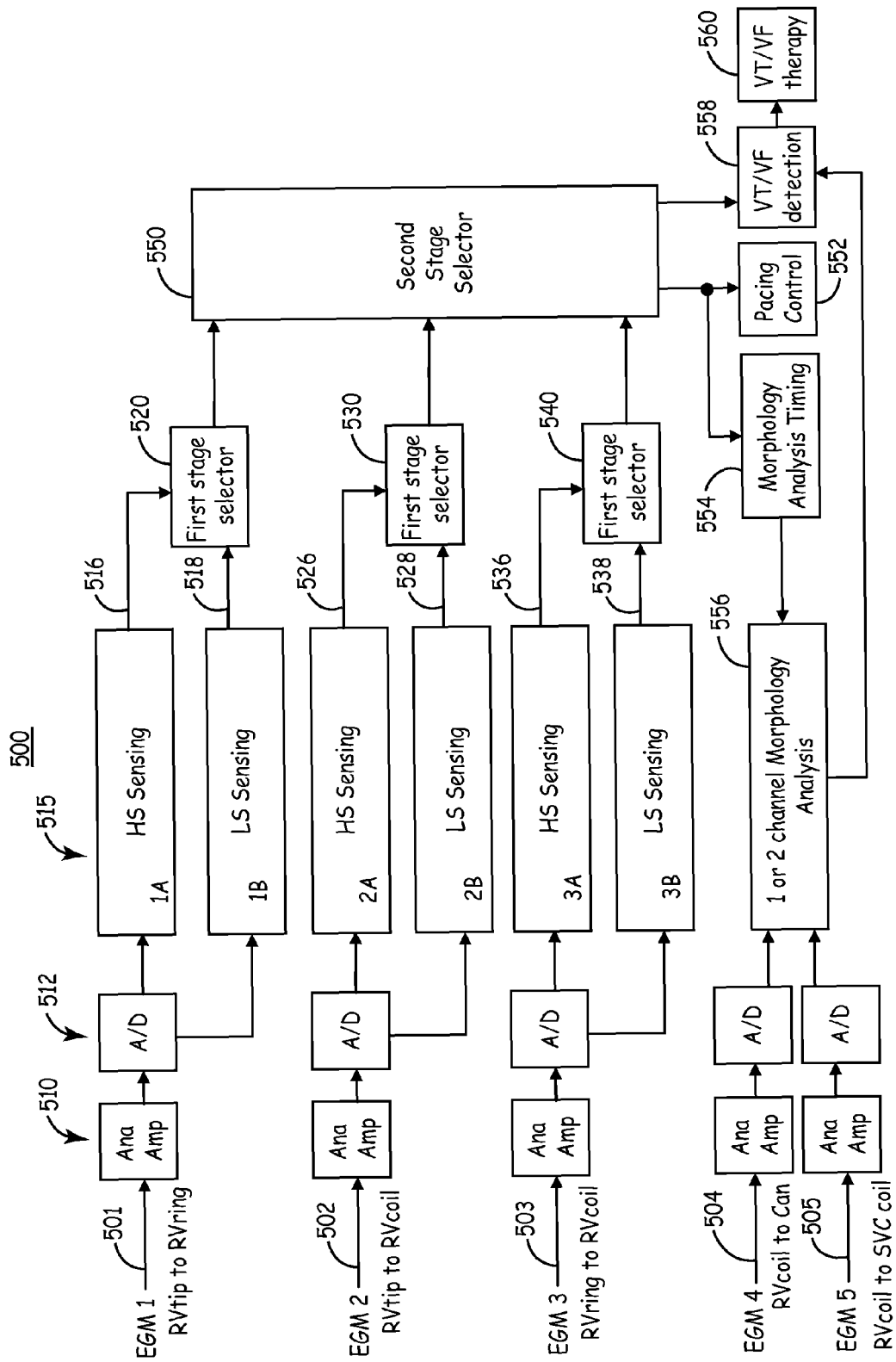
FIG. 7 is a functional block diagram of an illustrative embodiment of an ICD including multi-sensor, multi-channel signal processing.

FIG. 7 is a functional block diagram 500 of an illustrative embodiment of an ICD including multi-sensor, multi-channel signal processing. The ICD includes various EGM sensing electrode vectors, referred to as "sensors", 501 through 505 provided to a multi-channel signal processor including analog amplifiers 510, ND convertors 512, and multiple signal processing channels (1A-3A and 1B-3B) corresponding to sensors 501 through 503 and differentiated by channel sensitivity. The multi-channel processor further includes first stage selectors 520, 530 and 540 and a second stage selector 550 which receive the output signals 516, 518, 526, 528, 536, and 538 of the various processing channels. The first stage selectors 520, 530 and 540 and the second stage selector 550 cooperatively select which of the output signals are provided to controllers 554, 552, 558 and optionally 560. The controllers perform various ICD functions relating to arrhythmia detection and therapy delivery and include a morphology analysis timing control 554, pacing control 552, VT/VF detection 558, and VT/VF therapy control 560.

The embodiment shown illustrates the use of multiple sensing vector signals, i.e. multiple "sensor signals", obtained from an RV lead carrying a tip electrode, ring electrode, RV coil electrode and optionally an SVC coil electrode as described above. In this configuration, three "near-field" EGM signals 501, 502 and 503 and at least one "far-field" EGM signal 504, 505 are available. One near-field signal, EGM 1 501, is acquired by the "sensor" formed by the RV tip and RV ring bipolar pair. The other two near-field signals, EGM 2 502 and EGM 3 503, are acquired by the RV tip-to-RV coil "sensor", and the RV ring-to-RV coil "sensor", respectively.

The three near-field signals 501, 502, and 503 are provided to an analog amplifier bank 510 and respective ND convertors 512. The digital signals are each provided to respective multi-channel signal processors, referred to collectively by the reference numeral 515. The multi-channel signal processors 515 are shown here to each include two channels, one HS sensing channel 1A, 2A, or 3A and one LS sensing channel 1B, 2B, or 3B, however more sensing channels may be provided in each of the processors 515 as needed.

The outputs 516 and 518 of the signal processing channels 1A and 1B are provided to a first stage output selector 520. The first stage output selector 520 performs an analysis of the sensed event signals 516 and/or 518 received from the HS sensing and LS sensing channels 1A and 1B. Based on the analysis of the sensed event signals, the first stage selector makes a preliminary selection of which of the two outputs 516 and 518 from EGM 1 501 are to be provided as input to morphology analysis timing 554, pacing control 556 and/or VT/VF detection 558. In a similar manner, the first stage detectors 530 and 540 each make a preliminary selection regarding which of the HS sensing output 526, 536 and the LS sensing output 528, 538, respectively, are to be provided to morphology analysis timing 554, pacing control 556 and/or VT/VF detection 558.

In one embodiment, a default selection of sensed event signals is the output signal 516 (corresponding to RV tip-to-RV ring EGM 1 501 and processed by HS sensing 1A) provided as input to VT/VF detection 558. Output signal 518 (corresponding to RV tip-to-RV ring EGM 1 501 processed by LS sensing 1B) is the default selection provided as input to pacing control 552 and to morphology analysis timing 554. When the LS sensing output 518 provides sensed event signals that are determined to be stable in amplitude and rate, based on an analysis of sensed event amplitudes and sensed event intervals as described above, the default LS sensing output 518 is selected as input to pacing control 552. Pacing control 552 controls the delivery of pacing pulses in response to the sensed event output signal 518.

If first stage selector 520 determines that the LS sensing output signal 518 provides a threshold percentage of low amplitude events and/or fast event intervals, the first stage selector 520 will switch the output signal selection for input to pacing control 552 from the default selection 518 to the HS sensing output signal 516. This preliminary selection made by the first stage selector 520 is provided as input to second stage selector 550.

First stage selectors 530 and 540 may perform a similar analysis on the respective LS sensing output signals 528 and 538 to make a preliminary selection between HS output signals 526, 536 and LS output signals 528, 538 for use as the input to pacing control 552 and morphology analysis timing 554. The preliminary selected signals identified by first stage selectors 530 and 540 are provided to second stage selector 550.

The second stage selector 550 compares the preliminarily selected output signals from first stage selectors 520, 530, and 540. If the LS sensing output signal 518 is the preliminary selection for input to pacing control 552, this default selection may stand without further signal analysis. The default selection of HS sensing output 516 as input to VT/VF detection 558 may stand as well in view of the stable, reliable sensing found using this RV tip-to-RV ring sensor.

If the first stage selector 520 preliminarily selects the HS output 516 as input to pacing control 552, indicating that the LS output 518 included either low amplitude signals and/or fast RRIs, the second stage selector 550 analyzes the preliminarily selected signals from first stage selectors 520, 530 and 540 to determine if a better signal is available for use by pacing control 552 as well as for VT/VF detection 558 and morphology analysis timing 554. If the default signal 518 is not selected by first stage selector 520, then one of the other LS sensing output signals 528 and 538 may be selected for input to pacing control 552 and morphology analysis timing 554.

Noise or lead-related artifact may affect some sensors or channels without affecting other sensors or channels. Noise or lead-related artifact can produce high variability of sensed event amplitudes and/or sensed event intervals. The amplitude and event interval stability analysis performed by the first stage selectors 520, 530 and 540 will be sensitive to this variability. When such variability is present in both of the HS and LS sensing channels 1A and 1B of a default sensor 501, and the same or similar variability is not detected in both processing channels of another sensor 502 or 503, one of the output channels 526, 528, 536 or 538 of the other sensors 502 or 503 can be substituted for the default output signal.

If the electrical conductor associated any one electrode (RVtip or RVring or RVcoil), or the electrode itself, produces lead-related artifact, one of the three near-field sensing vectors (which excludes the electrode or conductor associated with artifact) will still provide adequate sensing. Oversensing due to lead-related artifact can be avoided. As such, if lead-related artifact arises from a single electrode or its associated conductor, two out of the three near-field EGM signals will be affected while one of the near-field EGM signals will be unaffected.

The first stage selectors of the two channels associated with the two affected EGM signals will preliminarily select the HS output signal for input to pacing control 552. The other first stage selector for the third channel that is unaffected by the single electrode or conductor causing lead-related artifact will preliminarily select the LS output signal. The second stage selector 550 will then select the LS output signal for input to pacing control 552 and the HS output signal, arising from the same EGM signal as the selected LS output signal, as input to VT/VF detection 558.

When compared to far-field EGM signals, such as RV coil to ICD housing or RV coil to SVC coil, the near-field EGM signal has a better signal to noise ratio and is generally less influenced by electromagnetic interference, muscle noise, or other non-cardiac noise. Thus substituting another near-field signal when a default near-field signal becomes noisy may provide better results for a particular device function then substituting a far-field signal. The multi-sensor, multi-channel signal processing of near-field signals can be used for LV sensing as well (LV tip to LVring and LV tip to RVcoil) and may be applicable in atrial sensing.

An analysis of sensed events performed by first stage selectors 520, 530 and 540 provides preliminary selection between HS and LS sensing channels for a given sensor. The second stage selector 550 performs further analysis and comparison of the first stage selected outputs to select a final output that is the most appropriate signal to be provided as input to VT/VF detection 558, pacing control 552 and morphology analysis timing 554.

Pacing control 552 may receive any one of the HS or LS sensing outputs 516, 518, 526, 528, 536, 538 at any given time based on an analysis of the stability of sensed event amplitudes and event intervals (or other event features). The selection process performed by first stage and second stage selectors 520, 530, 540 and 550 may include establishing a rate stability threshold and an amplitude stability threshold. The rate stability threshold and the amplitude stability threshold may be established as predetermined values, programmed values, or computed as a proportion of measured event amplitudes and event intervals, respectively. A rate and an amplitude determined from sensed event signals from each processing channel are compared to the established thresholds and a stability of the event amplitudes and a stability of the event rates is determined. The channel having the greatest stability may be selected for input to pacing control 552 and morphology analysis timing 554.

The HS sensing output signal, arising from the same sensor as the selected signal for pacing control, may be selected as input to VT/VF detection. It is generally desirable to use a higher sensitivity for sensing low amplitude fibrillation waves. At times, the HS sensing channel output may be used for both VT/VF detection 558 and pacing control 552. At other times, the selected input signal for pacing control 552 may be one of the LS sensing output signals 518, 528 or 538 and the input signal for VT/VF detection 558 is the HS sensing output signal 516, 526, and 536 corresponding to the same sensor. In this way, output signals arising from a sensor that is subjected to the least noise, least lead-related artifact or other potential causes of oversensing may be selected as the input signals to pacing control 552, morphology analysis timing 554 and VT/VF detection.

Morphology analysis timing 554 sets a time window relative to a sensed event during which the EGM signal morphology is analyzed for use in VT/VF detection. One or more digitized far-field EGM signals 504 and 505 are provided to morphology analysis 556. A morphology matching score may be computed by comparing the morphology of a sensed beat to a known morphology template. The morphology matching score is provided to VT/VF detection 558. It is generally desirable to use a far-field signal to perform morphology analysis because the far-field signal represents the spatial summation of action potential signals as they occur over a larger area of the ventricles than a near-field signal. The near-field signal, however, may provide more reliable event sensing for setting the morphology analysis time window. As such, morphology analysis timing 554 receives input from one of the near-field signals selected by second stage selector 350, which will generally be the same signal selected for input to pacing control 552.

VT/VF detection 558 receives a selected signal, typically a HS output signal 516, 526, or 536, from second stage selector for use in detecting VT or VF episodes. VT/VF detection 558 executes a detection algorithm, which may vary between embodiments so long as it utilizes measured intervals between events to detect VT or VF intervals. As mentioned previously, the input to VT/VF detection 558 may be selected as the HS output 516, 526 or 536 associated with the same sensor 501, 502, or 503 as the selected output signal provided to pacing control 552, which may be a HS or a LS output signal. In other embodiments, the selection of the signal provided to VT/VF detection 558 may be independent of the selection of the signal provided to pacing control 552.

When a VT/VF episode is detected, VT/VF detection 558 enables VT/VF therapy controller 560 for delivering a therapy as needed to treat the detected arrhythmia episode. While not shown explicitly in FIG. 7, second stage selector 550 may provide a selected output signal 516, 518, 526, 528, 536 and 538 from the multi-channel processor to VT/VF therapy controller 560 for use in controlling the timing of a delivered therapy.

Figure 8:
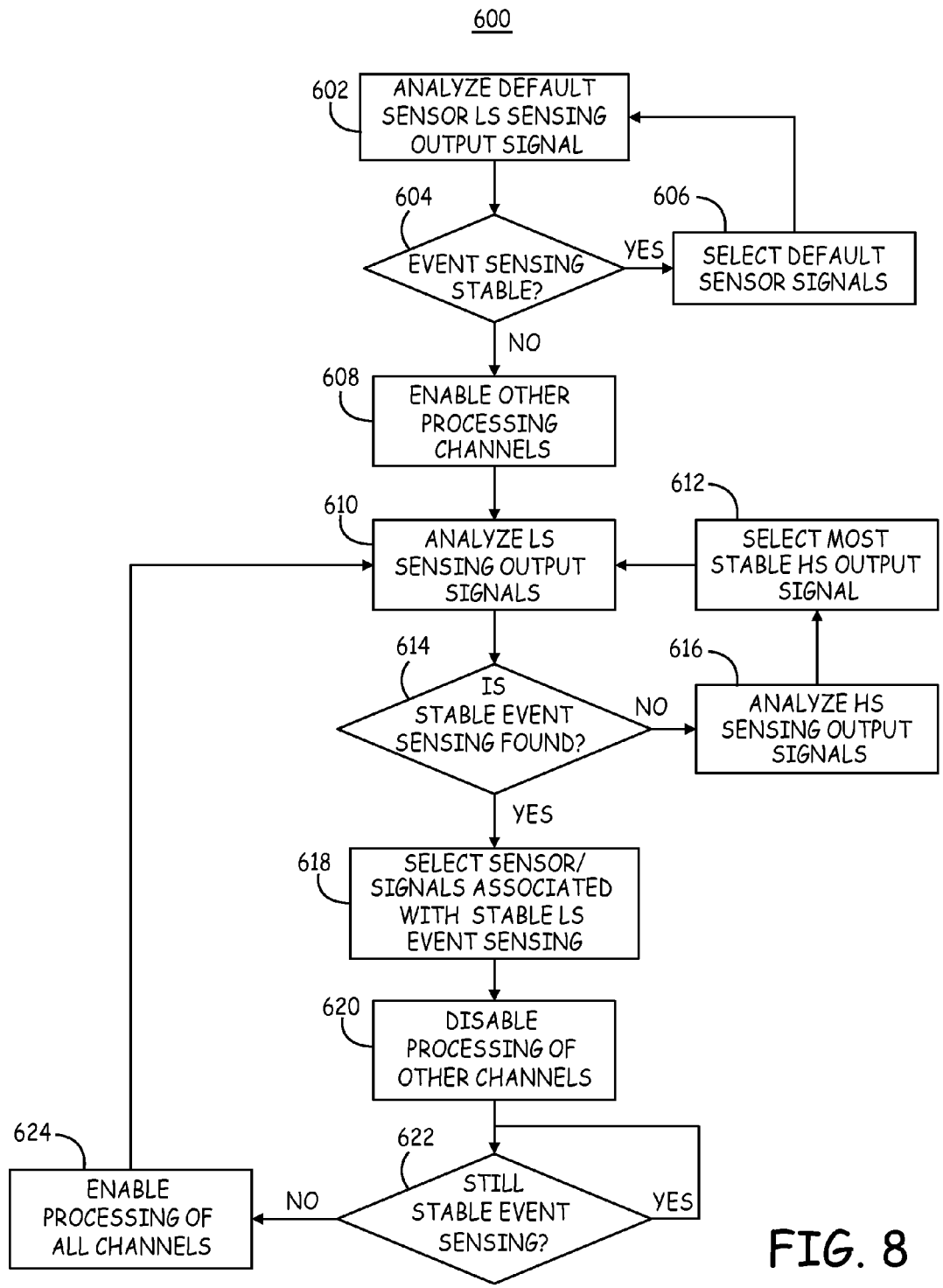
FIG. 8 is a flow chart of one method for selecting multi-channel signal processing output signals arising from multiple sensors in an IMD.

FIG. 8 is a flow chart 600 of one method for selecting multi-channel signal processing output signals arising from multiple sensors in an IMD. The method shown in FIG. 8 will be described with reference to the embodiment of the ICD shown in FIG. 7, however, the method is not limited to use with the ICD represented in FIG. 7 and may be used in any IMD system that includes multiple sensors.

At block 602, a default sensor is selected and the output of the LS sensing channel is analyzed at block 602. If sensed events on the LS sensing channel are found to be stable, for example in amplitude and rate as described above, default sensor output signals are selected at block 606 to be used as input to therapy control and detection controllers. With regard to the example of FIG. 7, the default EGM sensor is the RV tip-to-RV ring sensor. The default sensor signals to be used for pacing control and VT/VF detection are the LS sensing channel output and the HS sensing channel output, respectively. These default sensor signals are selected as input to pacing control and VT/VF detection at block 606 in response to the LS sensing output signal being stable. The process returns to block 602 to continue monitoring the LS sensing channel output signal for the default sensor.

If the default LS sensing channel output signal is not found to be stable at block 604, either initially or after selecting the default sensor signals at block 606 for a period of time, other processing channels associated with other sensors are enabled at block 608. As long as a default sensor is providing adequate signals, other multi-channel signal processors associated with other sensors may not need to be operating and consuming power. If the LS sensing channel output becomes variable in amplitude and/or rate, the other processing channels are enabled to determine if another EGM sensor provides a more reliable signal.

At block 610, the LS sensing channel output signals, associated with other available EGM sensors, are analyzed. If a LS sensing channel output signal is found to provide stable event sensing at block 614, the associated sensor may be selected for signal processing at block 618 with other processing channels associated with other sensors being disabled at block 620. The disabled sensor processing channels may be receiving a sensor signal that is noise corrupted. The LS sensing channel output signal found to be stable is selected as input to pacing control at block 618. The HS sensing channel output signal for the same sensor is selected as input to VT/VF detection at block 618.

At block 622, the selected LS sensing channel output signal continues to be monitored. As long as stable sensed event amplitudes and/or rates (or other selected features) are found, the other signal processing channels associated with other sensors remain disabled.

If the selected LS sensing channel output signal begins to increase in sensed event variability, the other sensor processing channels are enabled again at block 624. All of the LS sensing output signals are analyzed again at block 610 to select the LS sensing channel output signal providing the most reliable sensed event signal.

If none of the available LS sensing output signals are found to be stable at block 614, the default HS sensing channel output signal (associated with a default sensor) may be selected as input to both pacing control and VT/VF detection. Alternatively, all of the available HS sensing channel output signals from all available sensors may be analyzed at block 616. The most stable HS output channel signal is selected at block 612 to be provided as input to both pacing control and VT/VF detection.

After selecting a HS output signal for pacing control input, the LS channel output signal corresponding to the selected HS output signal is monitored and analyzed at block 610. Additionally, multi-channel signal processing may remain enabled for all sensors to allow analysis of all the LS channel output signals for all available EGM sensors. If any LS sensing channel output signal becomes stable, as determined at block 614, the ICD switches from using the HS sensing output signal as input to pacing control and VT/VF detection to using the stable LS sensing channel output signal as input to pacing control.

If the stable LS sensing channel output signal is associated with the same sensor as the currently selected HS sensing output signal, the current selection of the HS sensing output signal as input to VT/VF detection may remain unchanged t block 618. If the stable LS sensing channel output signal is associated with a different sensor than the currently selected HS sensing output signal, than the input to VT/VF detection may be switched from the currently selected HS sensing signal to the HS sensing output signal associated with the same sensor as the selected (stable) LS sensing signal.

In this way, the ICD may switch between EGM sensor signals and between multiple sensing channels for each EGM sensor, to obtain the most appropriate and most reliable event sensing for use in controlling an ICD function. It is recognized that in other embodiments, different default sensors, default sensing channel output signals, and different criteria for selecting a sensing output signal for use as input to an IMD controller may be defined according to the needs of a particular application.

Thus, a medical device and associated signal processing method have been presented in the foregoing description with reference to specific embodiments. It is appreciated that various modifications to the referenced embodiments may be made without departing from the scope of the disclosure as set forth in the following claims.

The invention claimed is:

1. A method for sensing a signal in an implantable medical device, comprising:
    acquiring a first physiological signal using a first implantable sensor;
    sensing the first physiological signal using a first sensing channel having a first sensitivity corresponding to a first amplitude setting;
    sensing the first physiological signal using a second sensing channel having a second sensitivity corresponding to a second amplitude setting, the second sensitivity higher than the first sensitivity;
    sensing a first plurality of events from the first sensing channel;
    measuring a feature from each of the first plurality of events;
    computing a stability metric of the first plurality of events from the features measured from each of the first plurality of events;
    selecting an output signal from one of the first sensing channel and the second sensing channel in response to the stability metric of the first plurality of events; and
    controlling a first therapy in response to the selected output signal.

2. The method of claim 1, further comprising detecting a physiological condition in response to an output signal of the second sensing channel.

3. The method of claim 2, further comprising:
sensing a second plurality of events from the second sensing channel;
detecting a fast rate in response to the second plurality of events;
setting a morphology analysis window in response to the selected output signal;
analyzing a signal morphology during the morphology analysis window; and
detecting the physiological condition in response to the morphology analysis and the fast rate.

4. The method of claim 3, further comprising sensing a second physiological signal using a second implantable sensor, wherein analyzing the signal morphology comprises:
applying the morphology analysis window to the second physiological signal; and
analyzing the signal morphology of the second physiological signal during the window.

5. The method of claim 1, further comprising:
measuring a feature of each of the first plurality of events; and
determining a stability of the measured features, wherein selecting the output signal comprises:
selecting the output signal from the first sensing channel in response to the measured features being determined to be stable; and
selecting the output signal from the second sensing channel in response to the measured features being determined to not be stable.

6. The method of claim 5, wherein the feature is one of an event interval and an event amplitude.

7. The method of claim 1, further comprising:
filtering the first physiological signal using a first filter in the first sensing channel; and
filtering the first physiological signal using a second filter in the second sensing channel, the second filter having different filtering properties than the first filter.

8. The method of claim 1, further comprising:
acquiring a second physiological signal using a second implantable sensor;
sensing the second physiological signal using a third sensing channel having a third sensitivity;
sensing a second plurality of events from the third sensing channel in response to selecting the output signal from the second sensing channel;
determining a stability of the second plurality of events; and
substituting an output signal of the third sensing channel for the selected output signal in response to determining the second plurality of events being stable.

9. The method of claim 8, further comprising:
sensing the second physiological signal using a fourth sensing channel having a fourth sensitivity greater than the third sensitivity; and
detecting a physiological condition in response to an output signal of the fourth sensing channel.

10. The method of claim 8, further comprising:
disabling the first sensing channel in response to selecting the third sensing channel;
monitoring stability of the plurality of second sensed events; and
re-enabling the first sensing channel in response to the plurality of second sensed events becoming unstable.

11. The method of claim 1, further comprising:
establishing a stability threshold;
comparing the stability metric to the stability threshold;
selecting the output of the second sensing channel as input to a pacing control module in response to the stability metric of the first plurality of events not meeting the stability threshold.

12. An implantable medical device for sensing a signal, comprising:
a first sensor to acquire a first physiological signal;
a digital signal processor configured to sense the first physiological signal and to sense a first plurality of events from the first physiological signal via a first signal processing channel having a first sensitivity corresponding to a first amplitude setting and a second signal processing channel having a second sensitivity corresponding to a second amplitude setting, the second sensitivity being higher than the first sensitivity;
a processor configured to measure a feature from each of the first plurality of events, compute a stability metric of the first plurality of events from the features measured from each of the first plurality of events, and select an output signal of one of the first channel and the second channel in response to the stability metric of the first plurality of events; and
a controller configured to control a therapy in response to the selected output signal.

13. The device of claim 12, further comprising a detector to detect a physiological condition in response to an output signal of the second sensing channel.

14. The device of claim 13, wherein the processor is further configured to sense a second plurality of events from the second sensing channel, and wherein the detector is configured to detect a fast rate in response to the second plurality of events, set a morphology analysis window in response to the selected output signal, analyze a signal morphology during the analysis window, and detect the physiological condition in response to the morphology analysis and the fast rate.

15. The device of claim 14, further comprising a second sensor to sense a second physiological signal, wherein the detector is further configured to apply the morphology analysis window to the second physiological signal and analyze the signal morphology of the second physiological signal during the window.

16. The device of claim 12, wherein the processor is further configured to measure a feature of each of the first plurality of events, determine a stability of the feature, and select an output of the first sensing channel in response to the feature being determined to be stable.

17. The device of claim 16, wherein the feature is one of an event interval and an event amplitude.

18. The device of claim 12, further comprising:
a first filter to filter the first physiological signal in the first sensing channel; and
a second filter to filter the first physiological signal in the second sensing channel, the second filter having different filtering properties than the first filter.

19. The device of claim 12, further comprising a second sensor to acquire a second physiological signal, wherein the processor is further configured to sense the second physiological signal via a third sensing channel having a third sensitivity, sense a second plurality of events from the third sensing channel in response to selecting the output signal from the second sensing channel, determine a stability of the second plurality of events, and substitute an output signal of the third sensing channel for the selected output signal in response to determining the second plurality of events being stable.

20. The device of claim 19, further comprising a detector detecting a physiological condition, wherein the processor is further configured to sense the second physiological signal via a fourth sensing channel having a fourth sensitivity, the fourth sensitivity higher than the third sensitivity, and wherein the detector detects the physiological condition in response to an output signal of the fourth sensing channel.

21. The device of claim 20, wherein the processor is further configured to disable the first sensing channel in response to selecting the third sensing channel, monitor the stability of the plurality of second sensed events, and re-enable the first sensing channel in response to the plurality of second sensed events becoming unstable.

\* \* \* \* \*